United States Patent [19]

Sato et al.

[11] Patent Number: 4,488,039

[45] Date of Patent: Dec. 11, 1984

[54] IMAGING SYSTEM HAVING VARI-FOCAL LENS FOR USE IN ENDOSCOPE

[75] Inventors: Masamichi Sato; Noboru Arai, both of Asaka; Yasumasa Sunaga, Omiya; Masafumi Inuiya, Asaka, all of Japan

[73] Assignees: Fuji Photo Film Co., Ltd., Kanagawa; Fuji Photo Optical Co., Ltd., Saitama, both of Japan

[21] Appl. No.: 414,957

[22] Filed: Sep. 3, 1982

[30] Foreign Application Priority Data

Sep. 12, 1981 [JP] Japan ................................. 56-144405

[51] Int. Cl.³ ............................................... G02B 5/14
[52] U.S. Cl. ................................... 250/216; 250/578; 350/429
[58] Field of Search ............... 250/201, 234, 216, 578; 350/429; 354/404; 355/55, 56; 128/4

[56] References Cited

U.S. PATENT DOCUMENTS 3,625,607 12/1971 Bravenec ............................ 355/56
3,860,935 1/1975 Stauffer ........................... 250/234 X
4,043,642 8/1977 Hirose et al. ..................... 350/429 X Primary Examiner—Edward P. Westin
Attorney, Agent, or Firm—Birch, Stewart, Kolasch & Birch

[57] ABSTRACT

An imaging system for use in an endoscope includes a vari-focal lens system provided in a viewing head to be inserted into a cavity or opening of a living body or machinery, a solid-state image sensor for imaging an image formed by the lens system to produce electrical signals representative of the image, a supporting unit for supporting the lens system and the image sensor thereon so as to change the spacing between the lens system and the image sensor on the optical axis of the lens system, and controller circuitry operable in response to magnification of the lens system for estimating the position of a focus of the lens system to control the supporting unit so as to position the image sensor substantially at the estimated position of the focus.

5 Claims, 3 Drawing Figures

IMAGING SYSTEM HAVING VARI-FOCAL LENS FOR USE IN ENDOSCOPE

BACKGROUND OF THE INVENTION

1. Field of the Invention

The present invention relates to generally an endoscope, and more specifically an imaging system for use in an endoscope, which system includes a solid-state imaging device picking up an image formed by a vari-focal lens.

2. Description of the Prior Art

It is well known that an endoscope is very useful for observing the inside of a cavity or opening of a living body or mechanical equipment. Proposed was an endoscope which employs a solid-state imaging device, such as a charge coupled device (CCD), and a bucket brigade device (BBD), generally known as a charge transfer device (CTD), rather than a so-called image guide consisting of a bundle of optical fibers.

In general, an endoscope employs conventionally a lens system having a relatively wide-angle viewing field so as to be larger in depth of focus, thus eliminating focus adjustment operations. An endoscope is however required that is equipped with a vari-focal lens such as a zoom lens. Such an endoscope generally includes a lens system composed of several groups of lenses, between which the spacings are adjustable to establish zooming effects. With an endoscope having an image bundle conveying optical image signals formed by a zoom lens, it is necessary to dispose the lens in such a position that the optical axis of the lens is substantially perpendicular to an imaging or focal plane of the fiber bundle. This requires that the position of the exit pupil of the zoom lens be far from the imaging end surface of the image bundle.

A zoom lens system for use conventionally in a still camera, a movie camera, or a television camera usually includes a focusing lens, and performs by itself variable magnification functions together with mechanical compensation functions for movement of the focal plane resultant from the former functions. Due to compactness in configuration of endoscopes, however, it is not advantageous for a zoom lens system for use in an endoscope to be equipped with the compensation functions by means of mechanical structure. In the case of an endoscope emplying an image bundle of optical fibers, it is also not advantageous to design its imaging system in such a manner that the image bundle is movable in dependence upon the operation of changing magnification of the zoom lens for compensation for the movement of the focus of the lens because of the lengthy structure of the bundle.

SUMMARY OF THE INVENTION

It is therefore an object of the present invention to provide an imaging system for use in an endoscope which is free from the above-mentioned disadvantages of the prior art.

In accordance with the invention, the object is accomplished by an imaging system for use in an endoscope comprising a vari-focal lens system provided in a viewing head to be inserted into a cavity, a solid-state imaging device for picking up an image formed by said lens system to produce electrical signals representative of the image, supporting means for supporting said lens system and imaging device thereon so as to change the spacing between said lens system and said imaging device on the optical axis of said lens system, and controller means operable in response to magnification of said lens system for estimating the position of a focus of said lens system to control said supporting means so as to position said imaging device substantially at the focus of said lens system.

The vari-focal lens system may comprise a zoom lens system having a movable lens for changing magnification of said zoom lens system.

The supporting means may comprise means for shifting at least one of said movable lens and said imaging device along the optical axis of said lens system.

The controller means may comprise a sensing circuit for sensing the position of said movable lens on the optical axis to estimate the position of the focus of said zoom lens system, and a driver circuit operative in response to said sensing circuit for driving said supporting means.

BRIEF DESCRIPTION OF THE DRAWINGS

The objects and features of the invention will become more apparent from a consideration of the following detailed description with reference to the accompanying drawings in which.

DETAILED DESCRIPTION OF THE PREFERRED EMBODIMENTS

Figure 1:
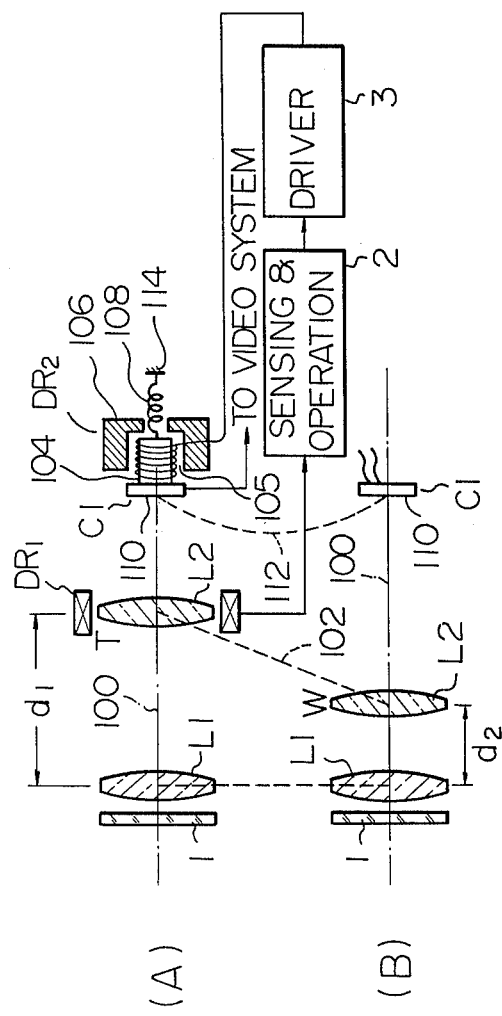
FIG. 1 shows schematically and partially in a block diagram a preferred embodiment of an imaging system for use in an endoscope in accordance with the present invention.

In FIG. 1, there is schematically illustrated an imaging system which is arranged within a viewing head of an endoscope, which may be inserted into a cavity or opening of a living body or a mechanical structure. For simplicity, the illustrative optical system of the viewing head is of a straight-viewing type, as an example. On the optical axis 100 of the optical system and behind a viewing window 1 with respect to an object (not shown) to be observed, there are disposed a stationary lens L1 and a movable lens L2 with a spacing d1 therebetween. In the vicinity of the focal plane of lenses L1 and L2 and on optical axis 100, a conventional solid-state imaging device or image sensor C1 is disposed, which may be a CTD, such as a CCD, BBD.

Lens L1 is affixed on a frame, not shown, of the viewing head, whereas lens L2 is movably supported by a driver arrangement DR1 so as to assume any position between its telephotographic position T shown in FIG. 1(A) and its wide-angle position W depicted in FIG. 1(B). Driver DR1 may be electromagnetic driving means, such as a solenoid, a rotary or linear motor, and also may include cams and/or hydraulic mechanism. Driver DR1 is adapted to be controlled from a manual control or operation unit (not shown) for the endoscope in response to manual operations.

FIG. 1(A) shows movable lens L2 at its telephotographic position T, while FIG. 1(B) shows lens L2 at its wide-angle position W, with the movement of lens L2 between both of those positions T and W illustrated by a dotted line 102 as the trace of the center of lens L2.

Solid-state imaging device C1 is supported by a moving coil 104 of another driver arrangement DR2 so as to be movable along the optical axis 100 of lenses L1 and L2. Moving coil 104 is located in a recess 105 of a permanent magnet 106, and attached to one end of a tension spring 108, of which the other end is stationarily affixed on a portion 114 of the frame of the viewing head in such a fashion that coil 104 is normally energized to move along optical axis 100 in the right hand direction in the figure. Therefore, moving coil 104, when energized, carries imaging device C1 along optical axis 100 in the left hand direction in the figure against the energizing force of spring 108. As driver system DR2, an electrical or hydraulic motor may also be useful, instead of the above-mentioned moving coil system, with gears and/or cams. It may however be advantageous to employ such a moving coil system from the viewpoint of capability of rapid and highly accurate movement of imaging device C1.

The endoscope shown in FIG. 1 includes a sensing and operation circuit 2, and a driver circuit 3, which may be arranged outside the viewing head thereof. Sensing and operation circuit 2 is connected to receive electrical signals from driver device DR1. In response to the signals from driver DR1, circuit 2 senses the position of lens L2 on its optical axis 100 to estimate or calculate an appropriate position for imaging device C1, which position is such that the imaging surface 110 of image-pickup device C1 is substantially on the focal plane of the zoom lens system including lens L1 and L2. Sensing and operation circuit 2 produces signals representative of the appropriate position of image sensor C1 to driver circuit 3, which in turn energizes and controls moving coil 104 so as to place image sensor C1 at the thus estimated appropriate position.

The appropriate positions of image sensor C1 which are calculated by circuit 2 between the telephotographic and wide-angle positions T and W are continuously plotted in the figure by a dotted line 112, as a trace of the center point of the imaging surface 110 of sensor C1. The curve 112 represents compensation for the movements of the focal plane of lenses L1 and L2 effected by zooming operations.

In the arrangement shown in FIG. 1, sensing and operation circuit 2 and driver circuit 3 are interconnected to adjust the position of image sensor C1 in response to the sensed position of lens L2. However, the arrangement may be designed to detect the position of imaging device C1 and estimate an appropriate position for lens L2, which is in turn translated to the estimated position by means of driver DR1.

In general, a zoom lens system for use in an endoscope may not be equipped with a focusing lens, that is commonly employed in a zoom lens system for use conventionally in a still camera, a movie camera, or a television camera, since a distance from the lens system of an endoscope to an object to be observed in a cavity or opening of a living body or machinery is relatively short and falls within a certain predetermined range of distance. The present invention may therefore be also applicable to a zoom lens system which does not include a focusing lens. It is to be noted that the driver arrangement including a moving coil is of course applicable to a zoom lens system having a focusing lens.

In accordance with the present invention, shifts of the focal plane of lenses L1 and L2 due to adjustment operations of magnification, i.e. zooming effect, will effectively be compensated for by transferring imaging device C1 to its appropriate position which is estimated by sensing and operation circuit 2 in response to the sensed position of lens L2. Imaging device C1 produces therefore video signals representative of a well-focused picture to an external video system.

Figure 2:
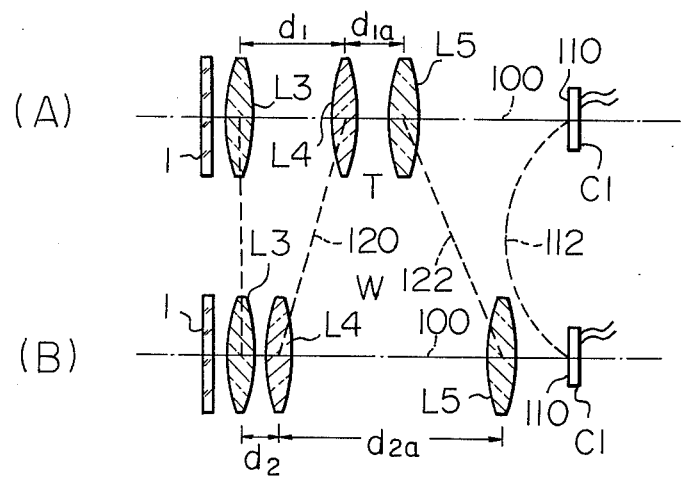
FIG. 2 shows schematically another embodiment of an imaging system in accordance with the invention.

FIG. 2 shows another embodiment in accordance with the present invention, in which the zoom lens system includes a stationary lens L3, and two movable lenses L4 and L5. FIG. 2(A) shows movable lenses L4 and L5 which are in their telephotographic position T with the distance between lenses L3 and L4 being d1, and the distance between lenses L4 and L5 kept d1a, as shown. In the case of wide-angle imaging as illustrated in FIG. 2(B), one movable lens L4 is positioned at the distance d2 from lens L3, while the other movable lens L5 is positioned at the distance d2a from lens L4. In other words, lenses L4 and L5 take the wide-angle positions W, as shown in FIG. 2(B). Between telephotographic and wide-angle positions T and W, movable lenses L4 and L5 may continuously take any intermediate position as depicted by dotted lines 120 and 122 in FIG. 2. Both movable lenses L4 and L5 may be transferred along optical axis 100 by driver means similar to driver DR1 of the embodiment shown in FIG. 1. It is to be appreciated that like components shown in FIG. 2 are designated by the same reference numerals as in FIG. 1. Although in FIG. 2 there are shown, for simplicity, neither driver means which are the same as or similar to driver arrangements DR1 and DR2 shown in FIG. 1, nor circuitry that is the same as or similar to circuits 2 and 3 of the FIG. 1 arrangement, it should be appreciated that lenses L4 and L5, and image sensor C1 are operatively connected to those means and circuitry.

In FIG. 2, solid-state image sensor C1 is supported by the same driver means as driver DR2 shown in FIG. 1, to be shiftable in position by means of driver circuit 3 under the control of sensing and operation circuit 2. As in the case of the arrangement shown in FIG. 1, image sensor C1 of the FIG. 2 embodiment is also movable so as to compensate for the movement of the focus of lenses L3, L4 and L5 resultant from zooming operations. The trace of the center of imaging surface 110 of imaging device C1 between telephotographic and wide-angle positions is also plotted by dotted line 112 in FIG. 2.

Figure 3:
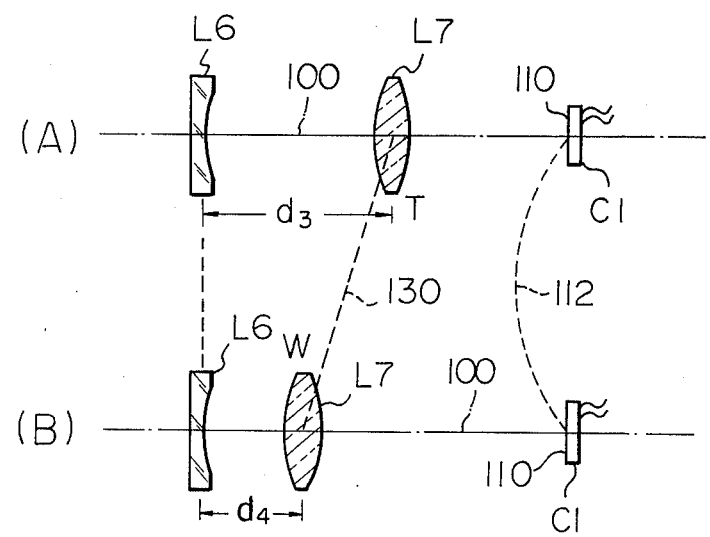
FIG. 3 illustrates a further embodiment of an imaging system in accordance with the present invention.

FIG. 3 shows still another embodiment in accordance with the present invention, in which stationary lens L6 is a planoconcave lens that is affixed to a portion of the frame of the endoscope viewing head, and partially functions as viewing window 1 of the embodiment shown in FIGS. 1 and 2. In the embodiment of the invention shown in FIG. 3, it should be noted that lens L7 and solid-state image sensor C1 are mechanically supported by driver means, such as driver arrangements DR1 and DR2, and electrically connected to circuits similar to sensing and operation circuit 2 and driver circuit 3, which are however not illustrated in FIG. 3 for simplicity.

As shown in FIG. 3(A), movable lens L7, which is also carried by the same means as driver DR1 of the FIG. 1 embodiment, takes its telephotographic imaging position T with the distance d3 maintained from fixed lens L6. Also as shown in FIG. 3(B), movable lens L3 takes its wide-angle imaging position W with the shorter spacing d4 from planoconcave lens L6. Movable lens L7 may of course take positions along a continuum between the telephotographic and wide-angle positions as depicted by the dotted line 130 in FIG. 3, in which the like constituent components are designated by the same reference numerals as in FIGS. 1 and 2.

In accordance with the present invention, as in the embodiments shown in FIGS. 1 and 2, imaging device C1 of the FIG. 3 arrangement is also supported by moving coil 104 of driver system DR2 so as to follow trace 112 in response to the zooming movement of lens L7 under the control of sensing and operation circuit 2.

In the illustrative embodiments shown in FIGS. 1, 2 and 3, movable lenses L2, L4, L5 and L7 are transferred linearly along optical axis 100. However, they may be carried in a non-linear fashion in dependence upon designing the lens system. Instead of such longitudinal movement of the lenses, lenses L1 through L7 may be a lens having surfaces of which the radius of curvature is variable, and which is fixed in position with respect to the frame of the viewing head. For example, they may be a lens which contains in a flexible enclosure a liquid transparent to light so as to establish a variable refraction index.

What we claim is:

1. An imaging system for use in an endoscope comprising:
    a vari-focal lens system provided in a viewing head to be inserted into a cavity;
    a solid-state imaging device for picking up an image formed by said lens system to produce electrical signals representative of the image;
    supporting means for supporting said lens system and imaging device thereon so as to change the spacing between said lens system and said imaging device on the optical axis of said lens system; and
    controller means operable in response to magnification of said lens system for estimating the position of a focus of said lens system to control said supporting means so as to position said imaging device substantially at the focus of said lens system.

2. An imaging system in accordance with claim 1, wherein said vari-focal lens system comprises a zoom lens system having a movable lens for changing magnification of said zoom lens system.

3. An imaging system in accordance with claim 2, wherein said supporting means comprises means for transferring at least one of said movable lens and said imaging device along the optical axis of said lens system.

4. An imaging system in accordance with claim 2, wherein said controller means comprises a sensing circuit for sensing the position of said movable lens on the optical axis to estimate the position of the focus of said zoom lens system, and a driver circuit operative in response to said sensing circuit for driving said supporting means.

5. An imaging system for use in an endoscope comprising:
    a zoom lens system provided in a viewing head to be inserted into a cavity, and having a movable lens;
    first supporting means for supporting said movable lens thereon movably along the optical axis of said zoom lens system for changing magnification of said zoom lens;
    a solid-state imaging device for picking up an image formed by said zoom lens system to produce electrical signals representative of the image;
    second supporting means for supporting said imaging device thereon movably along the optical axis of said zoom lens system;
    controller means for sensing the position of said movable lens to estimate the position of a focus of said zoom lens system; and
    driver means operative in response to said controller means for driving said second supporting means so as to position said imaging device substantially at the estimated position of the focus of said zoom lens system.

* * * * *